United States Patent [19]

Hastrup

[11] Patent Number: 5,036,002
[45] Date of Patent: Jul. 30, 1991

[54] EXPRESSION SYSTEM WITH TRANS-ACTING DNA SEGMENTS

[75] Inventor: Sven Hastrup, Copenhagen, Denmark

[73] Assignee: Novo-Nordisk A/S, Denmark

[21] Appl. No.: 39,298

[22] Filed: April 17, 1987

[30] Foreign Application Priority Data

Apr. 17, 1986 [DK] Denmark .............................. 1777/86

[51] Int. Cl.$^5$ ...................... C12P 21/06; C12P 19/34; C12N 15/00; C12N 1/22
[52] U.S. Cl. .................................... 435/69.1; 435/91; 435/172.3; 435/252.3; 435/252.31; 435/320.1; 435/832; 435/839; 536/27; 935/19; 935/29; 935/40; 935/56; 935/61; 935/72; 935/74
[58] Field of Search ............ 435/68, 91, 172.1, 172.3, 435/253, 320, 832, 839, 69.1, 252.3, 252.31; 536/27; 935/6, 9, 19, 27, 29, 40, 56

[56] References Cited

FOREIGN PATENT DOCUMENTS 0130074 2/1985 European Pat. Off. .
0182562 5/1986 European Pat. Off. .
9198978A 11/1984 Japan .
75286A 4/1985 Japan .

OTHER PUBLICATIONS

Imanaka et al, J. Bacteriology vol. 147, pp. 776-786 (1981).
Hayes The Genetics of Bacteria & Their Viruses 2 ed Blackwell Sci. Publ. pp. 713-729 (1968).
Rosenfeld et al, Mol Gen. Genet vol. 194 pp. 410-415 (1984).
Wilhelm, M. et al, Nucl. Acids Res. vol. 13, pp. 5717-5722 (1985).
Palva, et al., *Gene*, 22:229 (1983).
Ulmanen, et al., *J. Bacteriol*, 162:176 (1985).
Meyer and Fiechter, *Appl. Environ. Microbiol.* 50:503 (1985).
Yansura and Henner, *Proc. Natl. Acad. Sci. USA*, 81:439 (1984).
Roncero, *J. Bacteriol* 156:257 (1983).
Gilman and Chamberlain, *Cell* 35:285 (1983).
A copy of the European Search Report for Applicant's corresponding European Application No. 87303397.1.
Batt et al., *Can. J. Microbiol.* 31(10):930-933 (1985).
Workman et al., *CRC Critical Reviews in Biotech.* Issue 3:199-234 (1986).
Shamanna et al., *J. Bacteriol.* 139(1):71-79 (1979).
Gärtner et al., *J. Bateriol.* 170(7):3201-3109 (1988).
Wilhelm et al., *The Embo Journal* 3(11):2555-1560 (1984).

Primary Examiner—Robin Teskin
Assistant Examiner—Joan Ellis
Attorney, Agent, or Firm—Sterne, Kessler, Goldstein & Fox

[57] ABSTRACT

Gene expression systems comprising an expression vector and a "trans-acting DNA segment", where the expression vector comprises the gene or genes to be expressed and one or more cis-acting regulatory elements which are responsive to a trans-acting factor produced by said "trans-acting DNA segment". More specifically the invention relates to such gene expression systems where said "trans-acting DNA segment" and said cis-acting regulatory elements comprise one or more segments of the genome from a Bacillus species. Methods for stimulating the production of gene products, vectors for transforming microorganisms, and their use are also disclosed.

13 Claims, 9 Drawing Sheets

```
1start      12              24              36              48              60
GTGGATATGCT CATCAAACCTTT GTCAAAAAAGTA AATCAAAAGTA TTATTAAAAGAA
 V  D  I  A  D  Q  T  F   V  K  K  V    N  Q  K  L   L  L  K  E 72              84              96             108             120
ATCCTTAAAAAT TCACCTATTTCA AGAGCAAAATTA TCTGAAATGACT GGATTAAATAAA
 I  L  K  N  S  P  I  S   R  A  K  L   S  F  M  T   G  L  N  K 132            144             156             168             180
TCAACTGTCTCA TCACAGGTAAAC ACGTTAATGAAA GAAAGTATGGTA TTTGAAATAGGT
 S  T  V  S  S  Q  V  N   T  L  M  K   E  S  M  V   F  E  I  G 192            204             216             228             240
CAAGGACAATCA AGTGGCGGAAGA AGACCTGTCATG CTTGTTTTTAAT AAAAAGGCAGGA
 Q  G  Q  S  S  G  G  R   R  P  V  M   L  V  F  N   K  K  A  G 252            264             276             288             300
TACTCCGTTGGA ATAGATGTTGGT GTGGATTATATT AATGGCATTTTA ACAGACCTTGAA
 Y  S  V  G  I  D  V  G   V  D  Y  I   N  G  I  L   T  D  L  E
```

FIG. 8A

```
         312                 324                 336                 348                 360
GGAACAATCGTT CTTGATCAATAC CGCCATTTGGAA TCCAATTCTCCA GAAATAACGAAA
 G  T  I  V   L  D  Q  Y    R  H  L  E    S  N  S  P    E  I  T  K 372                 384                 396                 408                 420
GACATTTGATT GATATGATTCAT CACTTTATTACG CAAATGCCCCAA TCTCCGTACGGG
 D  I  L  I   D  M  I  H    H  F  I  T    Q  M  P  Q    S  P  Y  G 432                 444                 456                 468                 480
TTTATTGGTATA GGTATTTGCCGTG CCTGGACTCATT GATAAAGATCAA AAAATTGTTTTC
 F  I  G  I   G  I  C  V    P  G  L  I    D  K  D  Q    K  I  V  F 492                 504                 516                 528                 540
ACTCCGAACTCC AACTGGAGAGAT ATTGACTTAAAA TCTTCGATACAA GAGAAGTACAAT
 T  P  N  S   N  W  R  D    I  D  L  K    S  S  I  Q    E  K  Y  N 552                 564                 576                 588                 600
GTGTCTGTTTTT ATTGAAAATGAG GCAAATGCTGGC GCATATGGAGAA AAACTATTTGGA
 V  S  V  F   I  E  N  E    A  N  A  G    A  Y  G  E    K  L  F  G
```

FIG. 8B

```
612              624              636              648              660
GCTGCAAAAAT CACGATAACATT ATTTACGTAAGT ATCAGCCACAGGA ATAGGGATCGGT
 A  A  K  N   H  D  N  I   I  Y  V  S   I  S  T  G   I  G  I  G 672              684              696              708              720
GTTATTATCAAC AATCATTTATAT AGAGGAGTAAGC GGCTTCTCTGGA GAAATGGGACAT
 V  I  I  N   N  H  L  Y   R  G  V  S   G  F  S  G   E  M  G  H 732              744              756              768              780
ATGACAATAGAC TTTAATGGTCCT AAATGCAGTTGC GGAAACCGAGGA TGCTGGGAATTG
 M  T  I  D   F  N  G  P   K  C  S  C   G  N  R  G   C  W  E  L 792              804              816              828              840
TATGCTTCAGAG AAGGCTTTATTA AAATCTCTTCAG ACCAAAGAGAAA AAACTGTCCTAT
 Y  A  S  E   K  A  L  L   K  S  L  Q   T  K  E  K   K  L  S  Y 852              864              876              888              900
CAAGATATCATA AACCTCGCCCAT CTGAATGATATC GGAACCTTAAAT GCATTACAAAAT
 Q  D  I  I   N  L  A  H   L  N  D  I   G  T  L  N   A  L  Q  N
```

FIG. 8C

```
          912                924                936                948                960
TTTGGATTCTAT       TTAGGAATAGGC       CTTACCAATATT       CTAAATACTTTC       AACCCACAAGCC
 F  G  F  Y         L  G  I  G         L  T  N  I         L  N  T  F         N  P  Q  A 972                984                996               1008               1020
GTAATTTTAAGA       AATAGCATAATT       GAATCGCCATCCT       ATGGTTTAAAT       TCAATGAGAAGT
 V  I  L  R         N  S  I  I         E  S  H  P         M  V  L  N         S  M  R  S 1032               1044               1056               1068               1080
GAAGTATCATCA       AGGGTTATTCC       CAATTAGGCAAT       AGCTATGAATTA       TTGCCATCTTCC
 E  V  S  S         R  V  Y  S         Q  L  G  N         S  Y  E  L         L  P  S  S 1092               1104               1116               1128               1140
TTAGGACAGAAT       GCACCGGCATTA       GGAATGTCCTCC       ATTGTGATTGAT       CATTTTCTGGAC
 L  G  Q  N         A  P  A  L         G  M  S  S         I  V  I  D         H  F  L  D 1152    stop|
ATGATTACAAATG       TAA
 M  I  T  M
```

FIG. 8D

```
                    "-35"                              "-10"
1  AACTTTCTGAAAAGATGTTGAAAAGTCGAAAGGATTTTATAATATTAA
   GTCAAGTTAGTTTGTTTGATCAACAAACTAAT                        (P₁O₁)
   ━━━━━━━━━━━━━━━━━━━━━━━━━━━━━━━━
          ⬆

"-35"                              "-10"
   AAAAAACTAAAAAAAATATTGAAAATACTGACGAGGTTATATAAGATGAA
   AATAAGTTAGTTTGTTTAAACAACAAACTAAT                        (P₂O₂)
   ━━━━━━━━━━━━━━━━━━━━━━━━━━━━━━━━
          ⬆

(the arrows indicate the operators O₁ and O₂).
```

FIG. 9

EXPRESSION SYSTEM WITH TRANS-ACTING DNA SEGMENTS

BACKGROUND OF THE INVENTION

1. Field of the Invention

This invention relates generally to gene expression systems comprising an expression vector and a "trans-acting DNA segment" where the expression vector comprises the gene or genes to be expressed and one or more cis-acting regulatory elements which are responsive to a trans-acting factor produced by said "trans-acting DNA segment". More specifically the invention relates to such gene expression systems where said "trans-acting DNA segment" and said cis-acting regulatory elements comprise one or more segments of the genome from a Bacillus species.

2. Description of the Background Art

Gene expression systems, where the expression of a specific gene is regulated in the transcriptional phase by the binding of a repressor molecule to the DNA sequence comprising the operator for the gene concerned, thus preventing RNA polymerase from binding to the promotor, and in which induction occurs through the binding of an inducer to the repressor molecule, which causes a conformational shift in the repressor, decreasing the affinity of the repressor for the operator, are well known in *Eschericia coli*.

Such operator-repressor control systems as for example the lac operon therefore have for a number of years been used for the expression of foreign genes in *E. coli*.

Recently an interest has been raised for the cloning and expression of foreign genes in bacilli, especially *Bacillus subtilis*, for a number of reasons. In contrast to *E coli*, *B. subtilis* is not a pathogen, and it does not produce endotoxins. Also it possesses a secretory system that releases proteins into the culture medium in large quantities. Its genetic map is well characterized, and a great deal of information on large-scale cultivation of *B. subtilis* is available since the organism is widely used in industry. One disadvantage of *B. subtilis* strains, the formation of spores, has been circumvented by the development of asporogenic *B. subtilis* strains.

The gene expression systems hitherto known in bacilli that work on the transcriptional level are, however, not regulated by induction, but use a different mechanism. Gene regulation in these organisms is controlled by $\sigma$-factors, which are proteins that bind to the RNA polymerase and determine the recognition site for RNA initiation. Such systems cannot easily be used for the controlled expression of a foreign gene.

The attempts that have been made in expressing foreign genes in *B. subtilis* have until now concentrated on using α-amylase derived secretion vectors (Palva et al: Gene 22 (1983) 229–235; Ulmanen et al.: J. Bacteriol 162 (1985) 176–182; and Meyer and Fiechter: Appl. Environ. Microbiol. 50 (1985) 503–507).

One general problem with organisms that have cloned genes is the low expression of foreign or abnormal proteins. Gene expression depends on environmental conditions which determine cellular physiology. In many cases, optimal culture conditions for product formation are not identical with optimal growth conditions, and in some cases the foreign gene products may even be toxic to the host organism.

The results from the attempts to express foreign genes in bacilli mentioned above have indicated that either the regulation is performed on the translational level, or the foreign gene product is decomposed through the proteolytic action from exoenzymes native to *B. subtilis*. The yields of foreign proteins have therefore in these attempts been very variable.

In *E. coli* this problem has been alleviated by the use of inducible operator-repressor expression systems as those mentioned above.

Use of the lac repressor-operator from *E. coli* in *B. subtilis* has been reported by Yansura and Henner (Proc. Natl. Acad. Sci. U.S.A. 81 (1984) 439–443). This solution, however, suffers from the disadvantage that the lac operator-repressor system is not native to bacilli.

For a number of years it has been known that the production/occurrence of a number of enzymes in bacilli could be induced by xylose and other sugars in the growth medium, but the mechanism behind this phenomenon has remained unknown. The enzymes induced by xylose are those necessary for xylan utilization in bacilli such as described by I. G. Roncero, J. Bacteriol. 156 (1983) 257–263.

For a number of years it has also been known that this xylose induction only occurs when a suitable growth phase has been obtained by the culture, i.e., when the logarithmic growth phase has ceased and the culture has reached a certain maturity.

The structural gene for the production of xylanase has been cloned and used for the expression of xylanase in *E. coli* and *B. subtilis* (Japanese published patent No. 75286-A and 9198978-A).

BRIEF DESCRIPTION OF THE INVENTION

It has now surprisingly been found that the mechanism behind the induction of the production of xylan digesting enzymes in *B. subtilis* is of the operator-repressor type.

Further it has been possible to isolate the genes involved and determine the structure and base sequence of said operator-repressor expression system in the genome of *B. subtilis*.

This suggests further that the production of other enzymes that is induced by the addition of other sugars, also is governed by such operator-repressor systems.

Consequently the invention provides for a novel gene expression system comprising an expression vector and a trans-acting DNA segment, the expression vector comprising the gene or genes to be expressed and one or more cis-acting regulatory elements which are responsive to a trans-acting factor produced by said "trans-acting DNA, segment" and wherein said "trans-acting DNA segments" and cis-acting regulatory elements are obtainable from the genome of a Bacillus species.

In a second aspect the invention provides for a method for stimulating the production of a gene product, which comprises:

a) inserting a "trans-acting DNA segment" into a host, said "trans-acting DNA segment" being obtainable from the genome of a Bacillus species, which segment codes for a trans-acting factor;

b) inserting an expression vector into said host, said expression vector comprising the gene or genes coding for the gene product or products to be expressed and one or more cis-acting regulatory elements which are responsive to said trans-acting factor produced from said "trans-acting DNA segment";

c) cultivating the host; and if necessary d) at an appropriate time when the population of the host has reached a desirable level adding a compound that inactivates said trans-acting factor to the culture in order to derepress said cis-acting regulatory elements, and thereby initiate the production of said desired gene product or products.

In a third aspect the invention provides for a vector for use in expressing gene products, comprising DNA coding for the gene product or products and one or more cis-acting regulatory elements which respond to a trans-acting transcription factor which is coded for by a DNA segment obtainable from a Bacillus species, and which DNA segment may be included in the vector.

In a fourth aspect the invention provides for a vector for use in expressing gene products, comprising a DNA segment obtainable from a Bacillus species and coding for a trans-acting transcription factor which represses one or more cis-acting regulatory elements that are coupled to DNA coding for the gene product or products, and which DNA coding for the gene product or products and one or more cis-acting regulatory elements may be included in the vector.

In a fifth aspect the invention provides for novel microorganisms transformed with a vector according to the third or fourth aspect above.

In a sixth aspect the invention provides for the use of the novel gene expression system of the invention for the production of transformed microorganisms, and the use of such transformed microorganisms for the production of gene products heterologous to the original microorganism.

BRIEF DESCRIPTION OF THE DRAWING

The invention will be explained in more detail in the following with reference to the drawings, wherein

FIG. 8 shows the base sequence for the gene coding for the repressor xylR.

FIG. 9 shows the base sequence for the two promoter-operator sequences $P_1O_1$ and $P_2O_2$.

DETAILED DESCRIPTION OF THE INVENTION

Figure 1:
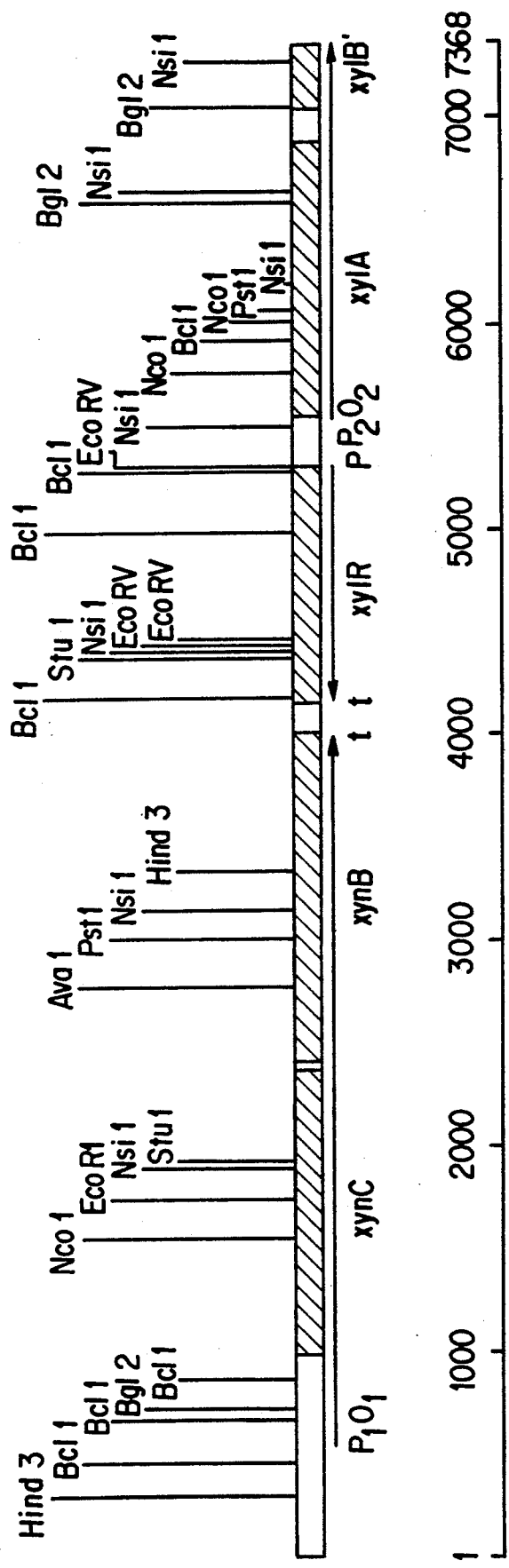
FIG. 1 shows the restriction map of the xylose regulon comprising the gene expression system of the invention.

As indicated above the invention relates in its first aspect to a novel gene expression system comprising an expression vector and a transacting DNA segment, the expression vector comprising the gene or genes to be expressed and one or more cis-acting regulatory elements which are responsive to a trans-acting factor produced by said "trans-acting DNA, segment" and wherein said "trans-acting DNA segments" and cis-acting regulatory elements are obtainable from the genome of a Bacillus species.

One system originates from *Bacillus subtilis* and comprises in its native state two cis-acting regulatory elements (promotor-operators) each regulating the transcription of two genes, and one DNA segment coding for a trans-acting factor (repressor gene) to which the two promotor-operators are responsive.

The system regulates the production of the enzymes necessary for the growth on xylose and xylose-polymers of *Bacillus subtilis*, and the repressor molecule is derepressed by the presence of xylose in the medium.

Because of the growth phase regulation it is, however, not necessary to omit the inducer molecule (xylose) from the growth medium, since the induction only occurs after the logarithmic growth phase has ended, and an appropriate population has been reached.

This allows for the system to be self regulating when used to transform bacilli, and xylose is included in the initial growth medium.

In the elucidation of the system it was surprisingly found that the repressor gene was situated between the two regulated operons, and that the transcription was in the opposite direction of the transcription of the two operons.

For the use of the system for the purposes of the invention it is not necessary to employ all of the elements described above, but only the repressor gene in connection with at least one of the promotors.

One embodiment of the system of the invention thus contemplates a gene expression system, wherein the expression vector comprises one cis-acting regulatory element which is responsive to said trans-acting factor.

In bacilli the repressor gene is already present, and it is consequently not necessary to insert the repressor gene in a vector used to transform bacilli.

In another embodiment the invention allows for the simultaneous production of at least two different heterologous gene products by employing an expression vector comprising two different cis-acting regulatory elements both of which are responsive to said trans-acting factor.

Although it is not necessary it is contemplated that for the use of the system in microorganisms other than *B. subtilis*, the "trans-acting DNA segment" is situated in the expression vector.

Also it has been found that the results obtained by transforming bacilli are superior when using expression vectors containing the repressor gene, so that the organism actually has several genes coding for the repressor.

In a number of experiments it has been shown that even though the repressor gene in the native system is transcribed in a direction opposite to the transcription of the two operons, the repressor functions no matter what the direction of transcription is.

The system has been shown to be operative also in microorganisms of other genera such as in *E. coli*, except that in such cases a promotor native to the pertinent microorganism must be inserted in front of the bacillus operator.

As mentioned above the structure and base sequence of the gene expression system of the invention for *B. subtilis* that is inducible with xylose has been determined, and thereby it was found that the gene coding for the repressor, xylR, has the base sequence shown in FIG. 8.

```
| start        12            24                36            48            60
GTGGATATCGCT  CATCAAACCTTT  GTCAAAAAAGTA      AATCAAAAGTTA  TTATTAAAAGAA
fM D  I  A    D  Q  T  F    V  K  K  V        N  Q  K  L    L  L  K  E
```

-continued

```
         72              84              96             108             120
ATCCTTAAAAAT    TCACCTATTTCA    AGAGCAAAATTA    TCTGAAATGACT    GGATTAAATAAA
  I  L  K  N      S  P  I  S      R  A  K  L      S  F  M  T      G  L  N  K 132             144             156             168             180
TCAACTGTCTCA    TCACAGGTAAAC    ACGTTAATGAAA    GAAAGTATGGTA    TTTGAAATAGGT
  S  T  V  S      S  Q  V  N      T  L  M  K      E  S  M  V      F  E  I  G 192             204             216             228             240
CAAGGACAATCA    AGTGGCGGAAGA    AGACCTGTCATG    CTTGTTTTTAAT    AAAAAGGCAGGA
  Q  G  Q  S      S  G  G  R      R  P  V  M      L  V  F  N      K  K  A  G 252             264             276             288             300
TACTCCGTTGGA    ATAGATGTTGGT    GTGGATTATATT    AATGGCATTTTA    ACAGACCTTGAA
  Y  S  V  G      I  D  V  G      V  D  Y  I      N  G  I  L      T  D  L  E 312             324             336             348             360
GGAACAATCGTT    CTTGATCAATAC    CGCCATTTGGAA    TCCAATTCTCCA    GAAATAACGAAA
  G  T  I  V      L  D  Q  Y      R  H  L  E      S  N  S  P      E  I  T  K 372             384             396             408             420
GACATTTTGATT    GATATGATTCAT    CACTTTATTACG    CAAATGCCCCAA    TCTCCGTACGGG
  D  I  L  I      D  M  I  H      H  F  I  T      Q  M  P  Q      S  P  Y  G 432             444             456             468             480
TTTATTGGTATA    GGTATTTGCGTG    CCTGGACTCATT    GATAAAGATCAA    AAAATTGTTTTC
  F  I  G  I      G  I  C  V      P  G  L  I      D  K  D  Q      K  I  V  F 492             504             516             528             540
ACTCCGAACTCC    AACTGGAGAGAT    ATTGACTTAAAA    TCTTCGATACAA    GAGAAGTACAAT
  T  P  N  S      N  W  R  D      I  D  L  K      S  S  I  Q      E  K  Y  N 552             564             576             588             600
GTGTCTGTTTTT    ATTGAAAATGAG    GCAAATGCTGGC    GCATATGGAGAA    AAACTATTTGGA
  V  S  V  F      I  E  N  E      A  N  A  G      A  Y  G  E      K  L  F  G 612             624             636             648             660
GCTGCAAAAAAT    CACGATAACATT    ATTTACGTAAGT    ATCAGCACAGGA    ATAGGGATCGGT
  A  A  K  N      H  D  N  I      I  Y  V  S      I  S  T  G      I  G  I  G 672             684             696             708             720
GTTATTATCAAC    AATCATTTATAT    AGAGGAGTAAGC    GGCTTCTCTGGA    GAAATGGGACAT
  V  I  I  N      N  H  L  Y      R  G  V  S      G  F  S  G      E  M  G  H 732             744             756             768             780
ATGACAATAGAC    TTTAATGGTCCT    AAATGCAGTTGC    GGAAACCGAGGA    TGCTGGGAATTG
  M  T  I  D      F  N  G  P      K  C  S  C      G  N  R  G      C  W  E  L 792             804             816             828             840
TATGCTTCAGAG    AAGGCTTTATTA    AAATCTCTTCAG    ACCAAAGAGAAA    AAACTGTCCTAT
  Y  A  S  E      K  A  L  L      K  S  L  Q      T  K  E  K      K  L  S  Y 852             864             876             888             900
CAAGATATCATA    AACCTCGCCCAT    CTGAATGATATC    GGAACCTTAAAT    GCATTACAAAAT
  Q  D  I  I      N  L  A  H      L  N  D  I      G  T  L  N      A  L  Q  N 912             924             936             948             960
TTTGGATTCTAT    TTAGGAATAGGC    CTTACCAATATT    CTAAATACTTTC    AACCCACAAGCC
  F  G  F  Y      L  G  I  G      L  T  N  I      L  N  T  F      N  P  Q  A 972             984             996            1008            1020
GTAATTTTAAGA    AATAGCATAATT    GAATCGCATCCT    ATGGTTTTAAAT    TCAATGAGAAGT
  V  I  L  R      N  S  I  I      E  S  H  P      M  V  L  N      S  M  R  S 1032            1044            1056            1068            1080
GAAGTATCATCA    AGGGTTTATTCC    CAATTAGGCAAT    AGCTATGAATTA    TTGCCATCTTCC
  E  V  S  S      R  V  Y  S      Q  L  G  N      S  Y  E  L      L  P  S  S 1092            1104            1116            1128            1140
TTAGGACAGAAT    GCACCGGCATTA    GGAATGTCCTCC    ATTGTGATTGAT    CATTTTCTGGAC
  L  G  Q  N      A  P  A  L      G  M  S  S      I  V  I  D      H  F  L  D 1152           stop |
ATGATTACAATG    TAA             (xylR)
  M  I  T  M
``` the two promoter-operator sequences, P₁O₁ and P₂O₂ are shown in FIG. 9.

```
                "-35"                              "-10"
 1
AACTTTCTGAAAAAGATGTTGAAAAAGTCGAAAGGATTTTATAATATTAA
GTCAAGTTAGTTTGTTTGATCAACAAACTAAT                  (P₁O₁)
     └─┐
       └─>
``` and

```
                 "-35"                              "-10"
AAAAAACTAAAAAAAATATTGAAAATACTGACGAGGTTATATAAGATGAA
AATAAGTTAGTTTGTTTAAACAACAAACTAAT                   (P₂O₂)
     └─┐
       └─>
```

(the arrows indicate the binding sites for the operators $O_1$ and $O_2$).

The structure of the regulon responsible for the transcription in *B. subtilis* of the genes necessary for growth on xylose was elucidated as follows:

Cloning

DNA from the *Bacillus subtilis* strain DN497 was digested partially with the restriction enzyme BglII and fragments from 2 to 10 kb were isolated from a 1% agarose gel. The DNA was then ligated with BamHI-cut, dephosphorylated plasmid pBR322 (from New England Biolabs), Beverly, Mass. and thereafter transformed into *E. coli* MC1000 r⁻m⁺. Selection was carried out on ampicillin plates and the transformants were sprayed with a 2 mM solution of 4-methyl-umbelleferyl-β-D-xyloside (from Sigma) Chemical Co., St. Louis, Mo.

Colonies carrying the xynB gene coding for the enzyme 1,4-β-D-xylosidase were detected as fluorescent when exposed to UV-light due to hydrolysis of the substrate.

The gene xynB was found on a 8.4 kb fragment, mapped more precisely, and sequenced. It was shown to be the last gene in a two-cistronic operon where the first gene (xynC) codes for a protein with long stretches of hydrophobic amino-acids.

In *E. coli* transcription of xynB was shown to originate partly from within xynC and partly from plasmid promoters. When cloned onto pDN1050 and transformed back into *B. subtilis* DN497 a strong transcription came from a 320 bp MspI-BglII fragment upstream of xynC.

DNA downstream of xynC was shown to repress this transcription but only in the absence of xylose. This indicated that a repressor gene (xylR) was present on the initial clone. SDS-page gel electrophoresis showed that the cloned DNA contained another gene that was regulated in the same way as xynB but transcribed from its own promoter. This was shown to be the gene coding for the enzyme xylose isomerase (xylA).

The xylR gene lies between xynB and xylA and is read from the other strand on the DNA (FIG. 1). The gene is 1152 bp long which means that the repressor monomer consists of 384 amino acids.

The two promoters controlled by the repressor were mapped by the enzyme S1 as described by Gilman and Chamberlain (1983), Cell, 35, 285-93.

The structure of the xylose regulon is shown on FIG. 1 which also contains a restriction map of the regulon, and wherein the direction of transcription is indicated with arrows.

In the following examples the promotor-operators $P_1O_1$ and $P_2O_2$, and the repressor gene xylR were used in the construction of a number of vectors used to transform various microorganisms in order to demonstrate the operativeness of the gene expression system of the invention. The examples are in no way to be construed as limiting the invention.

Also in the above text and in the examples below a number of microorganisms were used which are listed below:

METHODS

Preparation of plasmids and chromosomal DNA and transformation of *Bacillus subtilis* and *E. coli* were conducted according to the following general procedures. Digestion with restriction enzymes, Bal 31 nuclease treatment, oligo-DNA-linker insertion and ligation with T4-ligase of DNA were performed with enzymes from New England Biolabs under the conditions suggested by the supplier.

Strains

All *Bacillus subtilis* strains were derivatives of *Bacillus subtilis* 168 (Spizizen, Proc. Natl. Acad. Sci., 44: 1072-78, 1958). RUB200: aroI906, amyE07, amyR2 was obtained from Dr. Frank Young, University of Rochester, New York. SL438:trpC2 (sporulation and protease deficient) was obtained from Dr. Kim Hardy, Biogen, Geneve. DN497: amyE07, amyR2 is an aro⁺ transformant of RUB200 with chromosomal DNA from SL438, QB1133: aroI906, metB5, sacA321, amyE was from Dr. Georges Rapoport, IRBM, Paris. QB1130:dal, metB5, sacA331, amyE was obtained from the Bacillus Genetic Stock Center, Columbus, Ohio. DN608: dal-1, metB, sacA, amyE was an aro⁺, dal-1 transformant of QB1133 with chromosomal DNA from QB1130.

SHa28: metB, sacA, amyE, xynB, was made by congression into DN608 with chromosomal DNA from DN497 and that has a 4 bp deletion in xynB (a disrupted PstI site). SHa165: A protease weak nitrosoguanidine mutant of DN497.

*E. coli*: MC1000: F⁻ ΔlacX74 galF, galK, Δ(leu-ara)7697 (Casadaban, M. J., and Cohen, S. N. (1980), J. Mol. Biol. 7697, 138, 179-207). This strain was made r-m+ by conventional methods.

Plasmids

*E. coli* pBR322: Sutcliffe, J. G. (1979). Cold Spring Harbor Symp. Quant. Biol. 43, 77-90.

*B. subtilis* pDN 1050: Danish Patent Application No. 5940/84.

I. Transformation of B. subtilis

Competent *Bacillus subtilis* cells were prepared according to Yasbin et al. (J. Bacteriol. 121: 296-304, 1975). Cells were then harvested by centrifugation (7000 rpm, 3 min.), resuspended in one tenth volume of supernatant including 20% glycerol, frozen in liquid nitrogen and stored at −70° C. For transformation, frozen cells were thawed at 42° C. and mixed with one volume buffer (Spizizen's minimal medium (Spizizen, Proc. Natl. Acad. Sci. U.S.A. 44:1072-78, 1958)) with 0.4% glucose, 0.04M $MgCl_2$ and 0.002M EDTA). DNA was added and the mixture incubated with shaking at 37° C. for 20 min. Cells were then plated on appropriate selective media.

II. Transformation of E. coli

An overnight culture of *E. coli* K-12 strain No. 802 in LB (10 g Bacto tryptone, 5 g Bacto yeast extract and 10 g NaCl per liter water, pH 7.0) was diluted 100 fold in 500 ml LB and grown at 37° C. to $OD_{450} = 0.4$. The culture was chilled, left 15 min. on ice, spun for 15 min. at 3000 rpm (in a Sorvall GS3 rotor), resuspended in 200 ml cold 0.1M $CaCl_2$, left on ice for 20 min., spun for 10 min. at 3000 rpm, resuspended in 5 ml cold 0.1M $CaCl_2$ and left on ice for 20 hours. Cold glycerol was then added to 10% and aliquotes were frozen in liquid nitrogen and stored at −70° C. Frozen cells were thawed on ice, DNA was added, the mixture incubated 45 min. on ice, 2 min. at 37° C. and then plated on an appropriate selective medium.

III. Preparation of plasmids from E. coli

*E. coli* were grown overnight in 250 ml LB, 0.4% glucose and an appropriate antibiotic. Cells were harvested by centrifugation and resuspended in 4 ml Buffer 1 (0.025M Tris.HCl, pH=8.0, 0.01M EDTA, 0.05M glucose, 2 mg/ml lysozyme). The suspension was incubated at 0° C. for 15 min. and then mixed with 8 ml Buffer 2 (0.2M NaOH, 1% SDS). Then 6 ml Buffer 3 (3M NaAcetate, pH=4.8) was added, the mixture kept at 0° C. for 60 min. followed by centrifugation for 20 min. at 19000 rpm (ca. 45000 g in Sorvall SS34 rotor). The supernatant was precipitated with 0.6 vol cold isopropanol and resuspended in 1.2 ml 5TE (0.05M Tris.HCl, pH=8.0, 0.005M EDTA), plus 20 µl boiled RNase A (Boehringer) (2 mg/ml). 30 min. later the solution was layered on top of 4.0 ml Buffer 4 (80 g CsCl plus 56 ml 5TE) and 0.1 ml EtBr (10 mg/ml ethidium bromide) in a VTi65 tube. The mixture was centrifuged at 45000 rpm for 20 h. The plasmids were then removed from the tube, dialyzed and extracted as described in section VI.

IV. Preparation of plasmids from B. subtilis

Plasmids were prepared as described for *E. coli* strains (see section III) but with the following modifications. Growth was in LB including 0.01M potassium phosphate, pH=7.0 and an appropriate antibiotic (e.g. 6 µg/ml chloramphenicol and if required 100 µg/ml D-alanine. After harvest, cells were incubated at 37° C. with lysozyme. Buffer 2 was replaced by a mixture of one volume Buffer 2 and three volumes Buffer 5 (0.2M glycine, 0.2M NaCl and 1% SDS). The remaining steps were the same as in Section III.

V. Small scale preparation of plasmids from B. subtilis.

Plasmids from 5 ml *B. subtilis* in LB (including 0.01M phosphate pH=7.0 and appropriate antibiotics and D-alanine if required) were prepared as in section IV except 1: volumes of buffers were reduced four fold. 2: 0.5 ml phenol and 0.5 ml chloroform were added after Buffer 3. 3: After centrifugation at 19000 rpm, the supernatant was precipitated with ethanol, resuspended in 400 µl Buffer 6 (0.05M Tris.HCl pH=8.0, 0.1M NaAcetate), the plasmids were again precipitated, resuspended in 400 µl Buffer 6, precipitated, washed and resuspended in 100 µl TE (0.01M Tris.HCl, pH=8.0, 0.001M EDTA) with 1 µg/ml boiled RNase A (Boehringer).

VI. Preparation of chromosomal DNA from B. subtilis.

A pellet of frozen cells from about 50 ml culture was resuspended in 1.1 ml Buffer (0.05M Tris.HCl, pH=7.4, 0.1M NaCl, 25% sucrose). 100 µl lyzosyme (25 mg/ml) and 150 µl EDTA (0.5M, pH=8.0) were added. The mixture was incubated at 37° C. for 30 min. 2 ml 0.2% SDS were added followed by incubation for 30 min. at 37° C. 1 g CsCl and 0.05 ml EtBr (10 mg/ml) were added per 0.95 ml mixture and the mixture was centrifuged at 45000 rpm, 15° C., for 20 hours in a VTi65 rotor (Beckman).

The DNA was located under a long wave UV lamp and removed by puncturing the tube with a syringe. EtBr was extracted with isopropanol and the solution dialyzed for 2 hours against TEE (0.01M Tris.HCl, pH=8.0, 0.01M EDTA). The solution was then adjusted to 8 ml with TEE and extracted twice with phenol and once with chloroform. The DNA was precipitated with 0.1M NaCl and cold ethanol and dissolved in 1 ml TE (0.01M Tris.HCl, pH=8.0, 0.001M EDTA). The solution of chromosomal DNA was kept at 4° C.

EXAMPLES 1 AND 2

Two basic gene expression systems according to the invention were constructed into which different genes could be closed and expressed by either $P_1O_1$ and $P_2O_2$ under regulation from xylR.

Figure 2:
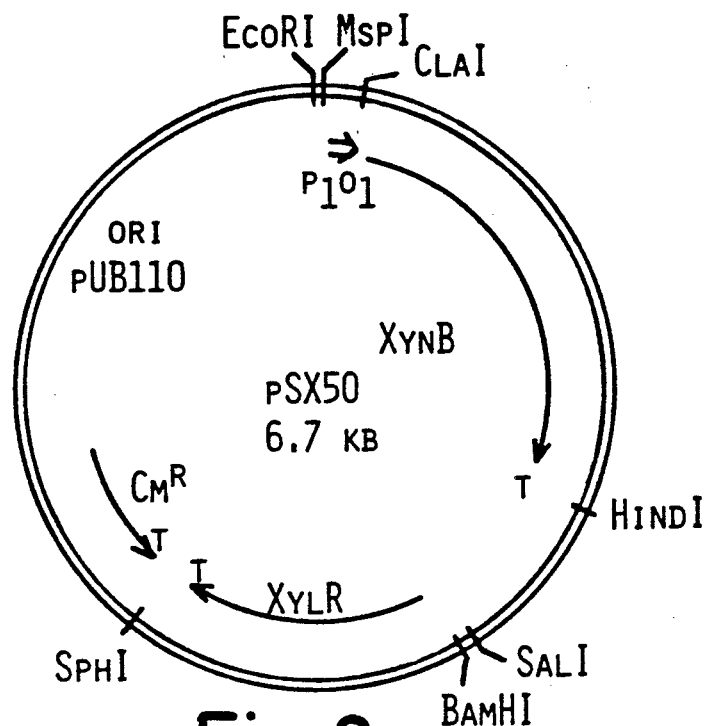
FIG. 2 shows the structure of a vector pSX 50 according to the invention.

In FIG. 2 a restriction map is shown of one of the basic vectors pSX 50 used in the following examples. As indicated in the figure it comprises the promotor-operator $P_1O_1$ on a 322MspI to BglII (converted to ClaI) fragment, a *B. pumilus* xynB gene on a 2.5 kb ClaI to SalI fragment, and the *B. subtilis* xylR gene on a 1380 bp BamHI to SphI fragment from 134 bp before the xylR start to 82 bp after its stop. The vector was inserted into the plasmid pDN 1050 (2.5 kb).

pSX 56

Figure 3:
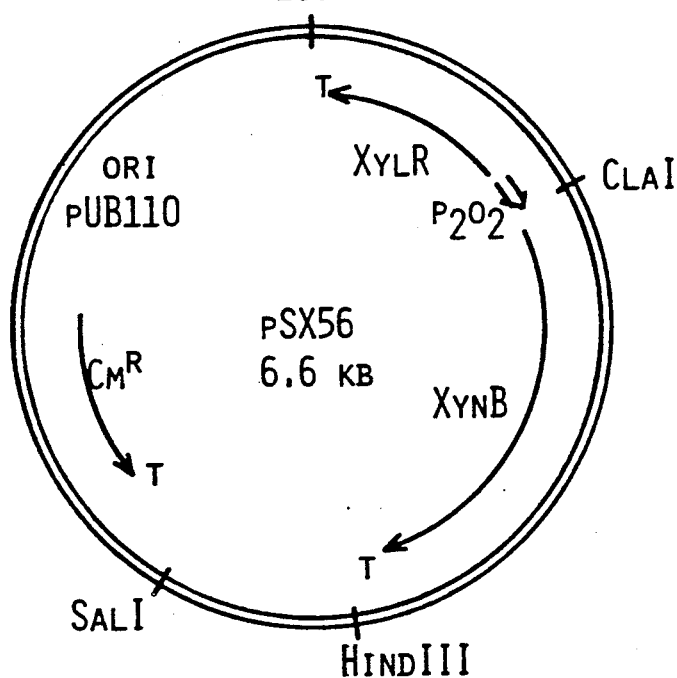
FIG. 3 shows the structure of another plasmid pSX 56 according to the invention, and, FIG. 4, 5, 6, and 7 show the structures of yet another four vectors according to the invention.

FIG. 3 shows the corresponding restriction map of the other basic vector pSX 56. As indicated it comprises the *B. subtilis* xylR gene and the promotor-operator $P_2O_2$ on a 1475 bp EcorI to ClaI fragment from 215 bp before the xylR start to 82 bp after its stop together with the same xynB gene as in pSX 50. This vector also was inserted into the plasmid pDN 1050 (2.65 kb).

*B. subtilis* SHa28 (xynB[31]) transformed with either of these two plasmids shows an increase by a factor of 150 to 200 in xylosidase activity as measured by the hydrolysis of p-nitro-phenyl-beta-D-xylopyranoside (Sigma), when grown on 0.2% xylose compared to growth without xylose.

EXAMPLE 3

Figure 4:
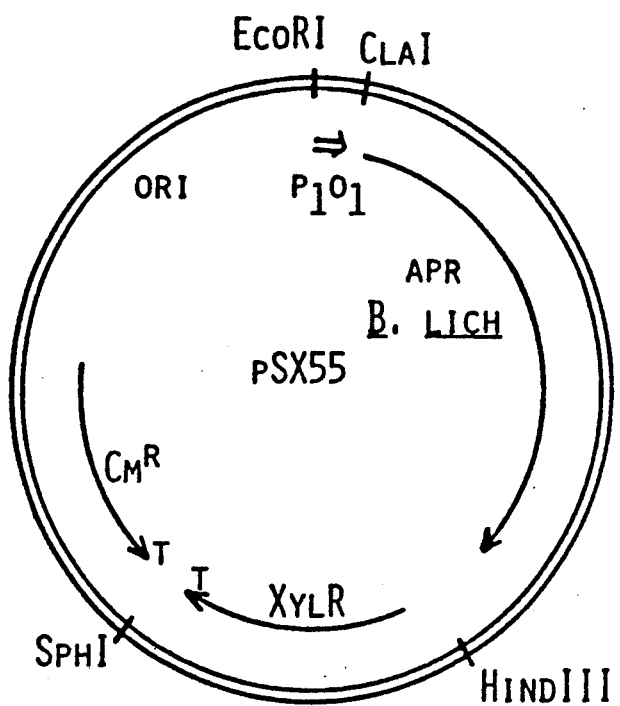

The xynB ClaI-BamH fragment on pSX 50 was replaced by the apr gene from *Bacillus licheniformis* coding for the extracellular alkaline protease subtilisin Carlsberg to obtain the plasmid pSX55 (FIG. 4).

In supernatants of SHa28 transformed with this plasmid grown with and without xylose, no substilisin band was seen without xylose, whereas it was the predominant band when the cells were grown in the presence of 0.2% xylose.

EXAMPLES 4 AND 5 pSX 52 and pSX 59

The calf prochymosin gene was fused to the *B. pumilus* xynB gene resulting in a gene that codes for a fusion protein that consists of the first 12 amino acids from xylosidase followed by prochymosin.

Figure 5:
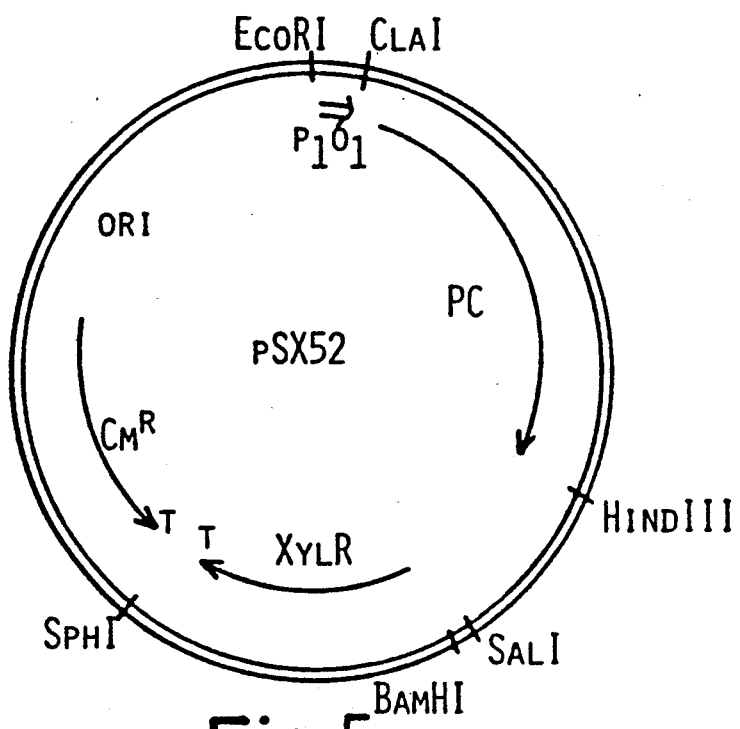
Figure 6:
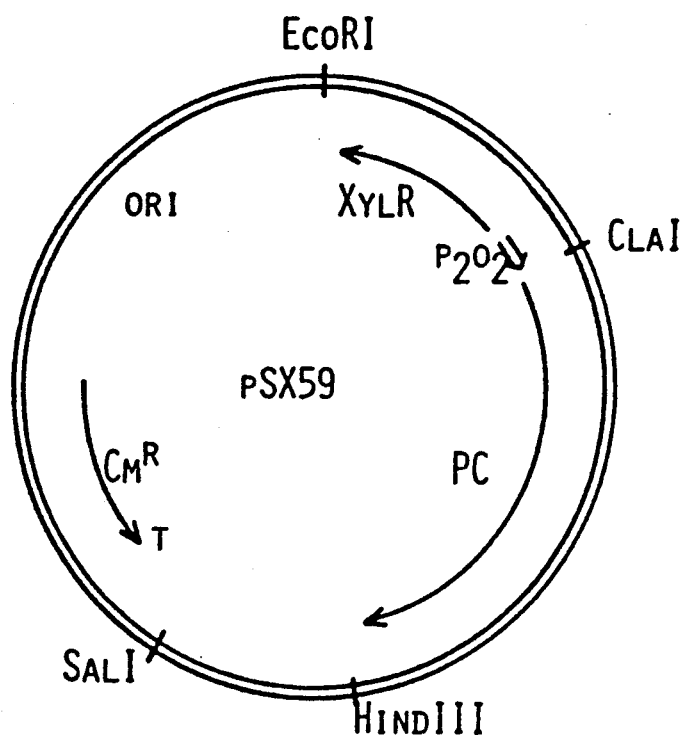

This fusion gene was cloned into ClaI-HindIII on pSX 50 and pSX 56 to obtain the plasmids pSX 52 and pSX 59 (FIGS. 5 and 6).

These plasmids were used to transform *B. subtilis* SHa 165 (DN 497 (protease(−)(nitrosoguanidine))).

The Western blot of intracellular fluid showed that the prochymosin gene is under xylose control.

EXAMPLE 6 pSX 62

Figure 7:
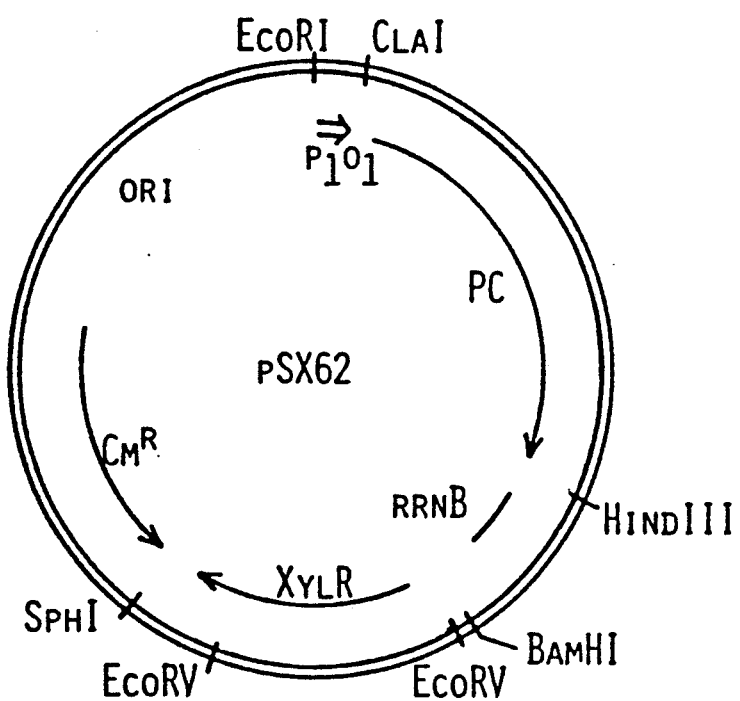

The *E. coli* rrnB terminator was cloned into pSX 52 behind the prochymosin gene to obtain the plasmid pSX 62 (FIG. 7) that was used to transform SHa 165. Western blot analysis showed that this increases the amount of prochymosin markedly (about 40% of total protein).

EXAMPLE 7 pSX 71

A deletion of 820 bp between the first and third EcoRV sites in the xylR gene in pSX 62 was performed to obtain a plasmid, pSX 71, wherein the xylR gene was destroyed. This plasmid was used to transform SHa 165. Western blot analysis clearly indicates that the production of prochymosin no longer is under xylose control.

What I claim:

1. A gene expression system comprising an expression vector having one or more negatively regulated promoter-operators, each operably linked to a gene to be expressed, said promoter-operators being under the control of a repressor protein encoded by a repressor gene, wherein said repressor gene is present on said expression vector or on a second expression vector, wherein said promoter-operators and repressor gene are derived from a Bacillus species, and wherein said repressor gene is xyl R and said promoter-operators are selected from the group consisting of xyn C, xyn B and xyl A, xyl B.

2. The gene expression system of claim 1 wherein said repressor gene has the sequence:

```
  start        12              24              36              48              60
GTGGATATCGCT  CATCAAACCTTT  GTCAAAAAAGTA  AATCAAAAGTTA  TTATTAAAAGAA
fM  D  I  A   D  Q  T  F    V  K  K  V    N  Q  K  L    L  L  K  E 72              84              96             108             120
ATCCTTAAAAAT  TCACCTATTTCA  AGAGCAAAATTA  TCTGAAATGACT  GGATTAAATAAA
 I  L  K  N   S  P  I  S    R  A  K  L    S  F  M  T    G  L  N  K 132             144             156             168             180
TCAACTGTCTCA  TCACAGGTAAAC  ACGTTAATGAAA  GAAAGTATGGTA  TTTGAAATAGGT
 S  T  V  S   S  Q  V  N    T  L  M  K    E  S  M  V    F  E  I  G 192             204             216             228             240
CAAGGACAATCA  AGTGGCGGAAGA  AGACCTGTCATG  CTTGTTTTTAAT  AAAAAGGCAGGA
 Q  G  Q  S   S  G  G  R    R  P  V  M    L  V  F  N    K  K  A  G 252             264             276             288             300
TACTCCGTTGGA  ATAGATGTTGGT  GTGGATTATATT  AATGGCATTTTA  ACAGACCTTGAA
 Y  S  V  G   I  D  V  G    V  D  Y  I    N  G  I  L    T  D  L  E 312             324             336             348             360
GGAACAATCGTT  CTTGATCAATAC  CGCCATTTGGAA  TCCAATTCTCCA  GAAATAACGAAA
 G  T  I  V   L  D  Q  Y    R  H  L  E    S  N  S  P    E  I  T  K 372             384             396             408             420
GACATTTTGATT  GATATGATTCAT  CACTTTATTACG  CAAATGCCCCAA  TCTCCGTACGGG
 D  I  L  I   D  M  I  H    H  F  I  T    Q  M  P  Q    S  P  Y  G 432             444             456             468             480
TTTATTGGTATA  GGTATTTGCGTG  CCTGGACTCATT  GATAAAGATCAA  AAAATTGTTTTC
 F  I  G  I   G  I  C  V    P  G  L  I    D  K  D  Q    K  I  V  F 492             504             516             528             540
ACTCCGAACTCC  AACTGGAGAGAT  ATTGACTTAAAA  TCTTCGATACAA  GAGAAGTACAAT
 T  P  N  S   N  W  R  D    I  D  L  K    S  S  I  Q    E  K  Y  N 552             564             576             588             600
GTGTCTGTTTTT  ATTGAAAATGAG  GCAAATGCTGGC  GCATATGGAGAA  AAACTATTTGGA
 V  S  V  F   I  E  N  E    A  N  A  G    A  Y  G  E    K  L  F  G 612             624             636             648             660
GCTGCAAAAAAT  CACGATAACATT  ATTTACGTAAGT  ATCAGCACAGGA  ATAGGGATCGGT
 A  A  K  N   H  D  N  I    I  Y  V  S    I  S  T  G    I  G  I  G
```

-continued

```
         672              684              696              708              720
GTTATTATCAAC     AATCATTTATAT     AGAGGAGTAAGC     GGCTTCTCTGGA     GAAATGGGACAT
V  I  I  N       N  H  L  Y       R  G  V  S       G  F  S  G       E  M  G  H 732              744              756              768              780
ATGACAATAGAC     TTTAATGGTCCT     AAATGCAGTTGC     GGAAACCGAGGA     TGCTGGGAATTG
M  T  I  D       F  N  G  P       K  C  S  C       G  N  R  G       C  W  E  L 792              804              816              828              840
TATGCTTCAGAG     AAGGCTTTATTA     AAATCTCTTCAG     ACCAAAGAGAAA     AAACTGTCCTAT
Y  A  S  E       K  A  L  L       K  S  L  Q       T  K  E  K       K  L  S  Y 852              864              876              888              900
CAAGATATCATA     AACCTCGCCCAT     CTGAATGATATC     GGAACCTTAAAT     GCATTACAAAT
Q  D  I  I       N  L  A  H       L  N  D  I       G  T  L  N       A  L  Q  N 912              924              936              948              960
TTTGGATTCTAT     TTAGGAATAGGC     CTTACCAATATT     CTAAATACTTTC     AACCCACAAGCC
F  G  F  Y       L  G  I  G       L  T  N  I       L  N  T  F       N  P  Q  A 972              984              996             1008             1020
GTAATTTTAAGA     AATAGCATAATT     GAATCGCATCCT     ATGGTTTTAAAT     TCAATGAGAAGT
V  I  L  R       N  S  I  I       E  S  H  P       M  V  L  N       S  M  R  S 1032             1044             1056             1068             1080
GAAGTATCATCA     AGGGTTTATTCC     CAATTAGGCAAT     AGCTATGAATTA     TTGCCATCTTCC
E  V  S  S       R  V  Y  S       Q  L  G  N       S  Y  E  L       L  P  S  S 1092             1104             1116             1128             1140
TTAGGACAGAAT     GCACCGGCATTA     GGAATGTCCTCC     ATTGTGATTGAT     CATTTTCTGGAC
L  G  Q  N       A  P  A  L       G  M  S  S       I  V  I  D       H  F  L  D

1152
ATGATTACAATG     TAA
M  I  T  M
``` and said promoter-operators comprise a sequence selected from the group consisting of

```
AACTTTCTGAAAAAGATGTTGAAAAAGTCGAAAGGATTTTATAATATTAA
GTCAAGTTAGTTTGTTTGATCAACAAACTAAT
``` and

```
AAAAAACTAAAAAAAATATTGAAAATACTGACGAGGTTATATAAGATGAA
AATAAGTTAGTTTGTTTAAACAACAAACTAAT.
```

3. The gene expression system of claim 1, wherein said expression vector comprises said repressor gene.

4. The gene expression system of claim 1, wherein said repressor gene is located in said second vector.

5. The gene expression system of claim 1, wherein said expression vector comprises said one or more promoter-operators each operably linked to a heterologous gene and wherein said repressor gene is present chromosomally in said Bacillus.

6. The gene expression system of claim 1, wherein said genes to be expressed are heterologous genes.

7. An expression vector comprising one or more negatively regulated promoter-operators each operably linked to a gene to be expressed, said promoter-operators being under the control of a repressor protein encoded by a repressor gene, wherein said repressor gene is present on said expression vector, wherein said repressor gene is xyl R, wherein said promoter-operators and repressor gene are derived from a Bacillus species and wherein said promoter-operators are selected form the group consisting of xyn C, xyn B and xyl A, xyl B.

8. The expression vector of claim 7 wherein said repressor gene has the sequence:

```
          12               24               36               48               60
    GTGGATATCGCT     CATCAAACCTTT     GTCAAAAAGTA     AATCAAAAGTTA     TTATTAAAAGAA
    fM D  I  A       D  Q  T  F       V  K  K  V       N  Q  K  L       L  L  K  E 72               84               96              108              120
    ATCCTTAAAAAT     TCACCTATTTCA     AGAGCAAAATTA     TCTGAAATGACT     GGATTAAATAAA
    I  L  K  N       S  P  I  S       R  A  K  L       S  F  M  T       G  L  N  K 132              144              156              168              180
    TCAACTGTCTCA     TCACAGGTAAAC     ACGTTAATGAAA     GAAAGTATGGTA     TTTGAAATAGGT
    S  T  V  S       S  Q  V  N       T  L  M  K       E  S  M  V       F  E  I  G 192              204              216              228              240
    CAAGGACAATCA     AGTGGCGGAAGA     AGACCTGTCATG     CTTGTTTTTAAT     AAAAAGGCAGGA
    Q  G  Q  S       S  G  G  R       R  P  V  M       L  V  F  N       K  K  A  G
```

```
           252              264              276              288              300
TACTCCGTTGGA   ATAGATGTTGGT   GTGGATTATATT   AATGGCATTTTA   ACAGACCTTGAA
Y  S  V  G     I  D  V  G     V  D  Y  I     N  G  I  L     T  D  L  E 312              324              336              348              360
GGAACAATCGTT   CTTGATCAATAC   CGCCATTTGGAA   TCCAATTCTCCA   GAAATAACGAAA
G  T  I  V     L  D  Q  Y     R  H  L  E     S  N  S  P     E  I  T  K 372              384              396              408              420
GACATTTTGATT   GATATGATTCAT   CACTTTATTACG   CAAATGCCCCAA   TCTCCGTACGGG
D  I  L  I     D  M  I  H     H  F  I  T     Q  M  P  Q     S  P  Y  G 432              444              456              468              480
TTTATTGGTATA   GGTATTTGCGTG   CCTGGACTCATT   GATAAAGATCAA   AAAATTGTTTTC
F  I  G  I     G  I  C  V     P  G  L  I     D  K  D  Q     K  I  V  F 492              504              516              528              540
ACTCCGAACTCC   AACTGGAGAGAT   ATTGACTTAAAA   TCTTCGATACAA   GAGAAGTACAAT
T  P  N  S     N  W  R  D     I  D  L  K     S  S  I  Q     E  K  Y  N 552              564              576              588              600
GTGTCTGTTTTT   ATTGAAAATGAG   GCAAATGCTGGC   GCATATGGAGAA   AAACTATTTGGA
V  S  V  F     I  E  N  E     A  N  A  G     A  Y  G  E     K  L  F  G 612              624              636              648              660
GCTGCAAAAAAT   CACGATAACATT   ATTTACGTAAGT   ATCAGCACAGGA   ATAGGGATCGGT
A  A  K  N     H  D  N  I     I  Y  V  S     I  S  T  G     I  G  I  G 672              684              696              708              720
GTTATTATCAAC   AATCATTTATAT   AGAGGAGTAAGC   GGCTTCTCTGGA   GAAATGGGACAT
V  I  I  N     N  H  L  Y     R  G  V  S     G  F  S  G     E  M  G  H 732              744              756              768              780
ATGACAATAGAC   TTTAATGGTCCT   AAATGCAGTTGC   GGAAACCGAGGA   TGCTGGGAATTG
M  T  I  D     F  N  G  P     K  C  S  C     G  N  R  G     C  W  E  L 792              804              816              828              840
TATGCTTCAGAG   AAGGCTTTATTA   AAATCTCTTCAG   ACCAAAGAGAAA   AAACTGTCCTAT
Y  A  S  E     K  A  L  L     K  S  L  Q     T  K  E  K     K  L  S  Y 852              864              876              888              900
CAAGATATCATA   AACCTCGCCCAT   CTGAATGATATC   GGAACCTTAAAT   GCATTACAAAAT
Q  D  I  I     N  L  A  H     L  N  D  I     G  T  L  N     A  L  Q  N 912              924              936              948              960
TTTGGATTCTAT   TTAGGAATAGGC   CTTACCAATATT   CTAAATACTTTC   AACCCACAAGCC
F  G  F  Y     L  G  I  G     L  T  N  I     L  N  T  F     N  P  Q  A 972              984              996             1008             1020
GTAATTTTAAGA   AATAGCATAATT   GAATCGCATCCT   ATGGTTTTAAAT   TCAATGAGAAGT
V  I  L  R     N  S  I  I     E  S  H  P     M  V  L  N     S  M  R  S 1032             1044             1056             1068             1080
GAAGTATCATCA   AGGGTTTATTCC   CAATTAGGCAAT   AGCTATGAATTA   TTGCCATCTTCC
E  V  S  S     R  V  Y  S     Q  L  G  N     S  Y  E  L     L  P  S  S 1092             1104             1116             1128             1140
TTAGGACAGAAT   GCACCGGCATTA   GGAATGTCCTCC   ATTGTGATTGAT   CATTTTCTGGAC
L  G  Q  N     A  P  A  L     G  M  S  S     I  V  I  D     H  F  L  D

1152
ATGATTACAATG   TAA
M  I  T  M
``` and wherein said promoter-operator comprises a sequence selected from the group consisting of:

AACTTTCTGAAAAAGATGTTGAAAAGTCGAAAGGATTTTATAATATTAAGTCAAGTTAGTTT
GTTTGATCAACAAACTAAT and AAAAAACTAAAAAAAATAAATTGAAAATACTGACGAGGTTATATAAGATGAAAATAAGTTAG
TTTGTTTAAACAACAAACTAAT.

9. The vector of claim 7 wherein said gene to be expressed is a heterologous gene.

10. A method for producing a gene product in a host, which comprises:

a) transforming or transfecting a host cell with the expression vector of claim 7;

b) cultivating said host under appropriate conditions to allow expression of said gene product in said host;

c) recovering said gene product from said culture.

11. The method of claim 10 wherein said repressor gene has the sequence:

```
           12              24              36              48              60
   GTGGATATCGCT    CATCAAACCTTT    GTCAAAAAGTA    AATCAAAAGTTA    TTATTAAAAGAA
   fM  D  I  A    D   Q  T  F     V  K  K  V     N  Q  K  L      L  L  K  E 72              84              96             108             120
   ATCCTTAAAAAT    TCACCTATTTCA    AGAGCAAAATTA    TCTGAAATGACT   GGATTAAATAAA
   I   L  K  N    S   P  I  S     R  A  K  L     S  F  M  T      G  L  N  K 132             144             156             168             180
   TCAACTGTCTCA    TCACAGGTAAAC    ACGTTAATGAAA    GAAAGTATGGTA   TTTGAAATAGGT
   S   T  V  S    S   Q  V  N     T  L  M  K     E  S  M  V      F  E  I  G 192             204             216             228             240
   CAAGGACAATCA    AGTGGCGGAAGA    AGACCTGTCATG    CTTGTTTTTAAT   AAAAAGGCAGGA
   Q   G  Q  S    S   G  G  R     R  P  V  M     L  V  F  N      K  K  A  G 252             264             276             288             300
   TACTCCGTTGGA    ATAGATGTTGGT    GTGGATTATATT    AATGGCATTTTA   ACAGACCTTGAA
   Y   S  V  G    I   D  V  G     V  D  Y  I     N  G  I  L      T  D  L  E 312             324             336             348             360
   GGAACAATCGTT    CTTGATCAATAC    CGCCATTTGGAA    TCCAATTCTCCA   GAAATAACGAAA
   G   T  I  V    L   D  Q  Y     R  H  L  E     S  N  S  P      E  I  T  K 372             384             396             408             420
   GACATTTTGATT    GATATGATTCAT    CACTTTATTACG    CAAATGCCCCAA   TCTCCGTACGGG
   D   I  L  I    D   M  I  H     H  F  I  T     Q  M  P  Q      S  P  Y  G 432             444             456             468             480
   TTTATTGGTATA    GGTATTTGCGTG    CCTGGACTCATT    GATAAAGATCAA   AAAATTGTTTTC
   F   I  G  I    G   I  C  V     P  G  L  I     D  K  D  Q      K  I  V  F 492             504             516             528             540
   ACTCCGAACTCC    AACTGGAGAGAT    ATTGACTTAAAA    TCTTCGATACAA   GAGAAGTACAAT
   T   P  N  S    N   W  R  D     I  D  L  K     S  S  I  Q      E  K  Y  N 552             564             576             588             600
   GTGTCTGTTTTT    ATTGAAAATGAG    GCAAATGCTGGC    GCATATGGAGAA   AAACTATTTGGA
   V   S  V  F    I   E  N  E     A  N  A  G     A  Y  G  E      K  L  F  G 612             624             636             648             660
   GCTGCAAAAAAT    CACGATAACATT    ATTTACGTAAGT    ATCAGCACAGGA   ATAGGGATCGGT
   A   A  K  N    H   D  N  I     I  Y  V  S     I  S  T  G      I  G  I  G 672             684             696             708             720
   GTTATTATCAAC    AATCATTTATAT    AGAGGAGTAAGC    GGCTTCTCTGGA   GAAATGGGACAT
   V   I  I  N    N   H  L  Y     R  G  V  S     G  F  S  G      E  M  G  H 732             744             756             768             780
   ATGACAATAGAC    TTTAATGGTCCT    AAATGCAGTTGC    GGAAACCGAGGA   TGCTGGGAATTG
   M   T  I  D    F   N  G  P     K  C  S  C     G  N  R  G      C  W  E  L 792             804             816             828             840
   TATGCTTCAGAG    AAGGCTTTATTA    AAATCTCTTCAG    ACCAAAGAGAAA   AAACTGTCCTAT
   Y   A  S  E    K   A  L  L     K  S  L  Q     T  K  E  K      K  L  S  Y 852             864             876             888             900
   CAAGATATCATA    AACCTCGCCCAT    CTGAATGATATC    GGAACCTTAAAT   GCATTACAAAAT
   Q   D  I  I    N   L  A  H     L  N  D  I     G  T  L  N      A  L  Q  N 912             924             936             948             960
   TTTGGATTCTAT    TTAGGAATAGGC    CTTACCAATATT    CTAAATACTTTC   AACCCACAAGCC
   F   G  F  Y    L   G  I  G     L  T  N  I     L  N  T  F      N  P  Q  A 972             984             996            1008            1020
   GTAATTTTAAGA    AATAGCATAATT    GAATCGCATCCT    ATGGTTTTAAAT   TCAATGAGAAGT
   V   I  L  R    N   S  I  I     E  S  H  P     M  V  L  N      S  M  R  S 1032            1044            1056            1068            1080
   GAAGTATCATCA    AGGGTTTATTCC    CAATTAGGCAAT    AGCTATGAATTA   TTGCCATCTTCC
   E   V  S  S    R   V  Y  S     Q  L  G  N     S  Y  E  L      L  P  S  S 1092            1104            1116            1128            1140
   TTAGGACAGAAT    GCACCGGCATTA    GGAATGTCCTCC    ATTGTGATTGAT   CATTTTCTGGAC
   L   G  Q  N    A   P  A  L     G  M  S  S     I  V  I  D      H  F  L  D
```

```
              1152
ATGATTACAATG  TAA
 M   I  T  M
``` and said promoter-operator comprises a sequence selected from the group consisting of 12. The method of claim 10 wherein said expression vector comprises said repressor gene.

13. The method of claim 10 wherein said gene to be expressed is a heterologous gene.

* * * * *

AACTTTCTGAAAAAGATG<u>TTGAAAAAGTCG</u>AAAGGATTTTA<u>TAATATTAA</u>
<u>G</u>TCAAG<u>TTAGTTTGTTT</u>GATC<u>AACAAACTAAT</u> and

AAAAAACTAAAAAAAATA<u>TTGAAAATACTG</u>ACGAGGTTATA<u>TAAGATGAA</u>
<u>A</u>ATAAG<u>TTAGTTTGTTT</u>AAAC<u>AACAAACTAA</u>T.